(12) United States Patent
Peyman (10) Patent No.: US 9,016,860 B2
(45) Date of Patent: Apr. 28, 2015

(54) FLUIDIC ADAPTIVE OPTIC FUNDUS CAMERA

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 0 days.

(21) Appl. No.: 13/793,199

(22) Filed: Mar. 11, 2013

(65) Prior Publication Data

US 2013/0211514 A1  Aug. 15, 2013

Related U.S. Application Data

(63) Continuation-in-part of application No. 13/165,231, filed on Jun. 21, 2011, now Pat. No. 8,409,278, which is a continuation-in-part of application No. 11/426,224, filed on Jun. 23, 2006, now Pat. No. 7,993,399, which is a continuation-in-part of application No. 11/259,781, filed on Oct. 27, 2005, now abandoned.

(51) Int. Cl.
| | | |
|---|---|---|
| *A61B 3/10* | (2006.01) | |
| *G02C 5/00* | (2006.01) | |
| *A61B 3/00* | (2006.01) | |
| *A61B 3/14* | (2006.01) | |
| *A61F 2/16* | (2006.01) | |
| *G02B 3/14* | (2006.01) | |
| *A61B 3/12* | (2006.01) | |

(52) U.S. Cl.
CPC .............. *A61F 2/1648* (2013.01); *A61F 2/1635* (2013.01); *G02B 3/14* (2013.01); *A61B 3/12* (2013.01); *A61B 3/1225* (2013.01); *A61F 2002/1651* (2013.01)

(58) Field of Classification Search
CPC .............. A61B 3/00; A61B 3/10; A61B 3/14; G02C 5/00; G02C 7/02; G02C 7/04
USPC ......... 351/200, 205–206, 210, 219, 222, 246, 351/41, 159, 160 R, 161, 176
See application file for complete search history.

(56) References Cited

U.S. PATENT DOCUMENTS

| | | |
|---|---|---|
| 4,373,218 A | 2/1983 | Schachar |
| 4,573,998 A | 3/1986 | Mazzocco |
| 4,685,921 A | 8/1987 | Peyman |
| 4,731,078 A | 3/1988 | Stoy et al. |

(Continued)

OTHER PUBLICATIONS

De-Ying Zhang, Nicole Justis, Yu-Hwa Lo, "Integrated Fluidic Adaptive Zoom Lens", Optics Letters, vol. 29, Issue No. 24, pp. 2855-2857, dated Dec. 15, 2004.

(Continued)

*Primary Examiner* — Dawayne A Pinkney
(74) *Attorney, Agent, or Firm* — The Law Office of Patrick F. O'Reilly III, LLC (57) ABSTRACT

A fundus camera includes three fluidic lenses, each fluidic lens having a chamber configured so as to capable of having a fluid inserted therein or removed therefrom, such that the shape of each of the three fluidic lenses is capable of being changed based on an amount of fluid therein, a refractive or diffractic telescopic system, a Shack-Hartmann sensor configured to automatically control of the amount of the fluid in the chamber of each of the three fluidic lenses, so as to be capable of correcting refractive errors in an eye, and a multifunction camera configured for precision of fundus photography.

19 Claims, 11 Drawing Sheets

(56) References Cited

U.S. PATENT DOCUMENTS

| | | | |
|---|---|---|---|
| 4,816,031 A | | 3/1989 | Pfoff |
| 6,142,630 A | * | 11/2000 | Koester ............ 351/219 |
| 6,186,628 B1 | * | 2/2001 | Van de Velde ........ 351/205 |
| 6,595,642 B2 | * | 7/2003 | Wirth ............... 351/211 |
| 6,673,067 B1 | | 1/2004 | Peyman |
| 6,806,988 B2 | | 10/2004 | Onuki et al. |
| 6,947,782 B2 | | 9/2005 | Schulman et al. |
| 7,182,780 B2 | | 2/2007 | Terwee et al. |
| 7,413,306 B2 | | 8/2008 | Campbell |
| 2002/0016629 A1 | | 2/2002 | Sandstedt |
| 2003/0147046 A1 | * | 8/2003 | Shadduck ............ 351/159 |
| 2005/0140922 A1 | * | 6/2005 | Bekerman et al. ........ 351/41 |
| 2006/0106426 A1 | * | 5/2006 | Campbell ............ 607/3 |
| 2007/0046948 A1 | * | 3/2007 | Podoleanu et al. ........ 356/497 |
| 2007/0156021 A1 | | 7/2007 | Morse et al. |
| 2007/0211207 A1 | * | 9/2007 | Lo et al. ............ 351/41 |
| 2008/0030682 A1 | | 2/2008 | Teige et al. |

OTHER PUBLICATIONS

First office action on the merits (Non-Final Rejection) in U.S. Appl. No. 14/461,263, mailed on Dec. 24, 2014.

* cited by examiner

FLUIDIC ADAPTIVE OPTIC FUNDUS CAMERA

This application is a continuation-in-part of application Ser. No. 13/165,231 entitled "External Lens with Flexible Membranes for Automatic Correction of the Refractive Errors of a Person", filed Jun. 21, 2011, which is a continuation-in-part of application Ser. No. 11/426,224 entitled "External Lens Adapted to Change Refractive Properties", filed Jun. 23, 2006, which is a continuation-in-part of application Ser. No. 11/259,781, entitled "Intraocular Lens Adapted for Accommodation Via Electrical Signals", filed Oct. 27, 2005, the entire contents of each of which are hereby incorporated by reference.

BACKGROUND

A normal emetropic eye includes a cornea, lens and retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal emetropic eye, or a cornea or lens having a refractive power stronger than that of the cornea and lens of an emetropic eye. This stronger refractive power causes the far point to be projected in front of the retina.

Conversely, a hypermetropic or hyperopic eye has an axial length shorter than that of a normal emetropic eye, or a lens or cornea having a refractive power less than that of a lens and cornea of an emetropic eye. This lesser refractive power causes the far point to be focused in back of the retina.

An eye suffering from astigmatism has a defect in the lens or shape of the cornea. Therefore, an astigmatic eye is incapable of sharply focusing images on the retina.

An eye can also suffer from presbyopia. Presbyopia is the inability of the eye to focus sharply on nearby objects, resulting from loss of elasticity of the crystalline lens.

Optical methods are known which involve the placement of lenses in front of the eye, for example, in the form of glasses or contact lenses, to correct vision disorders. A common method of correcting myopia is to place a "minus" or concave lens in front of the eye in order to decrease the refractive power of the cornea and lens. In a similar manner, hypermetropic or hyperopic conditions can be corrected to a certain degree by placing a "plus" or convex lens in front of the eye to increase the refractive power of the cornea and lens. Lenses having other shapes can be used to correct astigmatism. Bifocal lenses can be used to correct presbyopia. The concave, convex or other shaped lenses are typically configured in the form of glasses or contact lenses.

SUMMARY

In one embodiment, a lens system is provided. The lens system includes a lens adapted to be positioned along the main optical axis of the eye and a control unit. The control unit is operable with the lens to alter the focal length of the lens based at least partly upon a condition, such that the lens alters light rays and focuses the rays on the retina of the eye.

In another embodiment, a lens is provided. The lens includes a chamber adapted to house a substance. The lens is adapted to be positioned externally and relative to an eye and coupled to a control unit. The control unit is operable to control the focal length of the lens by influencing the substance, such control of the focal length altering light rays and focusing the light rays on the retina of the eye.

In another embodiment, a control unit is provided. The control unit includes an electronic circuit. The control unit is coupled to a lens, which includes a chamber adapted to house a substance. The lens is adapted to be positioned externally and relative to an eye. The electronic circuit is operable to control the focal length of the lens, such control of the focal length altering light rays and focusing the light rays on the retina of the eye.

Additional features and advantages are described herein, and will be apparent from, the following Detailed Description and the figures.

DETAILED DESCRIPTION

In various embodiments, a lens capable of accommodation in response to electrical signals is provided. The lens can be placed at any suitable location along the optical path of an eye, including but not limited to within the capsular bag, in place of the capsular bag, within the posterior chamber or on, in or behind the cornea. Further, it should be noted that any suitable section of the capsular bag can be removed, including but not limited to an anterior portion or a posterior portion around the main optical axis of the eye. The lens is preferably coupled to a fluidic pumping system which is also coupled to a control system which preferably includes a power source and a signal generation unit.

Figure 1:
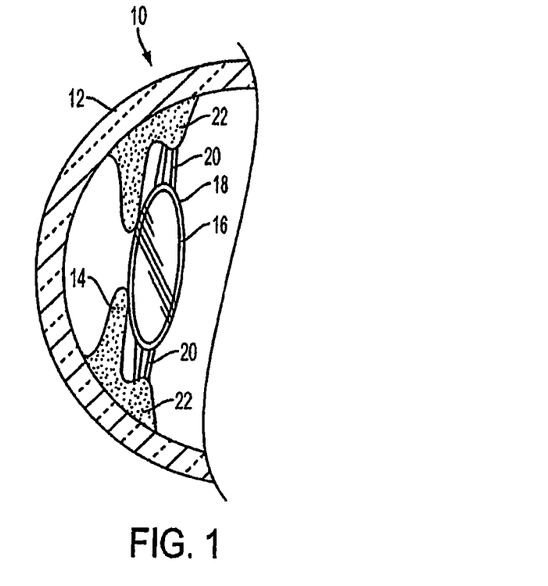
FIG. 1 is a side elevational view in section taken through the center of an eye showing the cornea, pupil, crystalline lens, and capsular bag.

Referring initially to FIG. 1, a normal eye 10 has a cornea 12, an iris 14, and a crystalline lens 16. The crystalline lens 16 is contained within a capsular bag 18 that is supported by zonules 20. The zonules 20, in turn, are connected to the ciliary muscle 22. According to Helmholz's theory of accommodation, upon contraction of the ciliary muscle 22, the tension on the zonules 20 is released. The elasticity of the lens causes the curvature of the lens 16 to increase, thereby providing increased refractive power for near vision. Conversely, during dis-accommodation, the ciliary muscle 22 is relaxed, increasing the tension on the zonules 20 and flattening the lens 16 to provide the proper refractive power for far vision.

Figure 2:
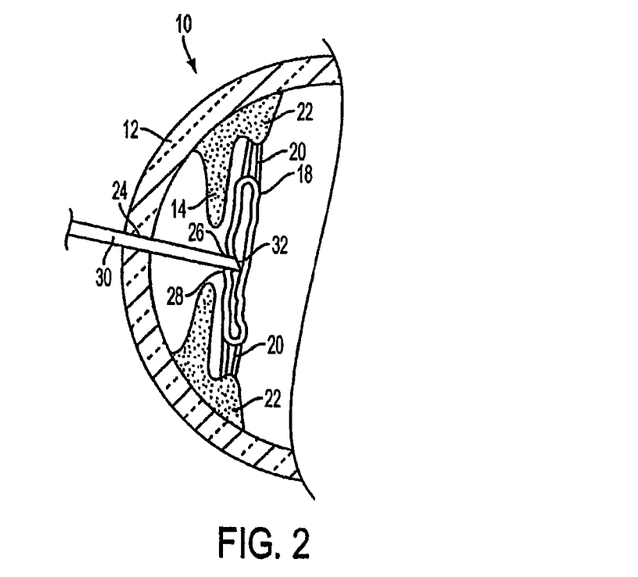
FIG. 2 is a side elevational view in section of the eye shown in FIG. 1 showing the capsular bag after removal of the crystalline lens.

If the electrically accommodating lens is to be positioned within the capsular bag and, thus, replace the crystalline lens, a suitable first step is to remove the existing lens. As illustrated in FIG. 2, the lens is preferably removed using any technique which allows removal of the lens through a relatively small incision, preferably about a 1-2 mm incision. The preferred method is to create a relatively small incision 24 in the cornea 12 and then perform a capsulorhexis to create an opening 26 into the anterior side 28 of the capsular bag 18. An ultrasonic probe 30 is inserted into the capsular bag 18 through the opening 26. The probe's vibrating tip 32 emulsifies the lens 16 into tiny fragments that are suctioned out of the capsular bag by an attachment on the probe tip (not shown). Alternatively, the lensectomy may be performed by laser phacoemulsification or irrigation and aspiration.

Once the crystalline lens 16 has been removed, the capsular bag 18 can be treated to help prevent a phenomenon known as capsular opacification. Capsular opacification is caused by the proliferated growth of the epithelial cells on the lens capsule. This growth can result in the cells covering all or a substantial portion of the front and rear surfaces of the lens capsule, which can cause the lens capsule to become cloudy and thus adversely affect the patient's vision. These cells can be removed by known techniques, such as by scraping away the epithelial cells; however, it is often difficult to remove all of the unwanted cells. Furthermore, after time, the unwanted cells typically grow back, requiring further surgery. To prevent capsular opacification, the capsular bag 18 is preferably treated to eliminate the proliferated growth of epithelial cells, as described below.

Figure 3:
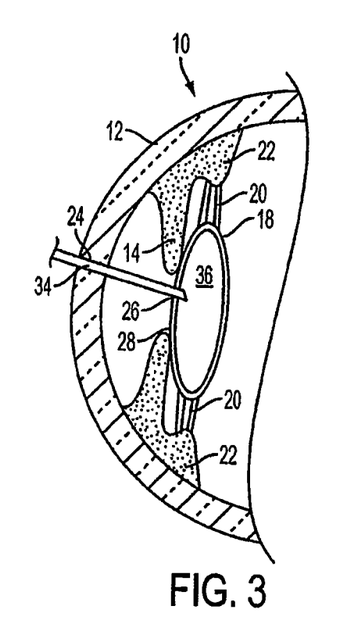
FIG. 3 is a side elevational view in section of the eye shown in FIG. 2 showing the treatment of the interior of the capsular bag with a liquid to prevent capsular opacification.

As seen in FIG. 3, one method of treating the epithelial cells to prevent capsular opacification is to use a cannula 34 to introduce a warm liquid 36 (preferably about <60° C.) into the capsular bag 18, filling the capsular bag 18. The liquid contains a suitable chemical that kills the remaining lens cells in the capsular bag and also cleans the interior of the capsular bag. Suitable chemicals, as well as other suitable methods of treatment that prevent capsular opacification are disclosed in U.S. Pat. No. 6,673,067 to Peyman, which is herein incorporated by reference in its entirety.

Figure 4:
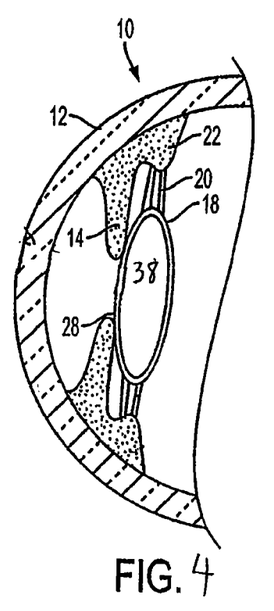
FIG. 4 is a side elevational view in section of the eye shown in FIG. 3 showing placement of a replacement lens into the capsular bag.
Figure 5:
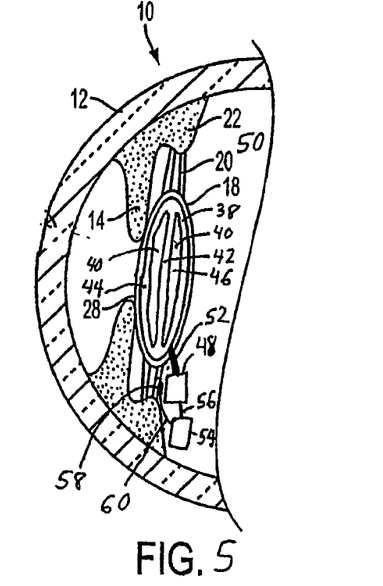
FIG. 5 is a side elevational view in section of the eye shown in FIG. 3 in which a replacement lens is positioned in the capsular bag and a fluidic system and remote power unit are positioned in the posterior chamber.

As shown in FIG. 4, a replacement lens 38 is then positioned within the capsular bag 18. Preferably, the lens 38 can be folded or rolled and inserted through the incision in the capsular bag 18; however, the lens 38 can be rigid and/or can be inserted through a larger second incision in the capsular bag 18 or the initial incision, possibly after the initial incision is widened, or in any other suitable manner. Preferably the lens 38 varies its focal length in response to changes in fluidic pressure within the lens made in accordance with electrical signals; however the lens 38 can change its index of refraction or alter its focal length in any other suitable manner. Since the capsular bag 18 is still in place, the capsular bag can still assist in accommodation; however, it is not necessary for capsular bag 18 to assist with accommodation. The lens, as shown in FIG. 5, preferably includes two chambers 40 set on opposite sides of a substrate 42 and covered with a flexible membrane 44; however, the lens can have one or any other suitable number of chambers. Preferably, the two chambers 40 contain a fluid 46, and preferably the fluid 46 is a sodium chromate solution; however, if desired, one or more of the chambers can contain something other than a fluid or the chambers can contain different fluids or different sodium chromate solutions. The substrate 42 is preferably glass; however, the substrate 42 can be any suitable material. Preferably, the flexible membrane 44 is a biocompatible material; however, the flexible membrane can be any suitable material.

Preferably, the fluidic pressure within the chambers 40 can be altered using a fluidic system 48 which includes a miniature fluidic pressure generator (e.g., a pump or any other suitable device), a fluid flow control device (e.g., a valve or any other suitable device), a control circuit and a pressure sensor; however, the fluidic pressure can be altered in any suitable manner. Further, if desired, a fluidic system 48 does not need a pressure sensor. When subjected to electrical signal, the electronic control circuit of the fluidic system 48 controls the valves and pumps to adjust the fluidic pressure in one or more of the chambers 40. Preferably, the fluidic pressure is adjusted by pumping fluid in or releasing a valve to allow fluid to flow out and back into the system 48; however, the fluidic pressure can be adjusted by pumping fluid out or in any other suitable manner. As a result, the shape and the focal length of the lens 38 is altered, providing accommodation. Lenses that similarly change focal length in response to fluidic pressure changes made in accordance with electrical signals are described in greater detail in "Integrated Fluidic Adaptive Zoom Lens", *Optics Letters*, Vol. 29, Issue 24, 2855-2857, December 2004, the entire contents of which is hereby incorporated by reference.

As shown in FIG. 5, fluidic system 48 is preferably positioned in the posterior chamber 50; however, the fluidic system 48 can be positioned outside the eye, within the sclera, between the sclera and the choroids or any other suitable location. Further, the fluidic system 48 is preferably positioned such that it is not in the visual pathway. A tube 52 fluidly connects the lens 38 and the fluidic system 48. Preferably, the tube 52 passes through a small incision in the capsular bag 18 near the connection of the zonules 20 and the capsular bag 18; however, the tube 52 can pass through the capsular bag in any suitable location.

Preferably, fluidic system 48 includes a power source which is preferably rechargeable through induction or other suitable means such as generating and storing electrical energy using eye and/or head movement to provide the energy to drive the generator; however, fluidic system 48 can be connected to a remote power source 54 as shown in FIG. 5 or to any other suitable power source. Preferably, the remote power source 54 is located in the posterior chamber 50; however, the remote power source 54 can be positioned outside the eye (e.g., under the scalp, within a sinus cavity, under the cheek, in the torso or in any other suitable location), within the sclera, between the sclera and the choroids or any other suitable location. Further, the remote power source 54 is preferably positioned such that it is not in the visual pathway. The remote power source 54 is preferably electrically coupled to the fluidic system 48 by electrically conductive line 56; however, the remote power source 54 can be coupled to the fluidic system 48 in any suitable manner. Further, the remote power source 54 preferably includes a signal generator which can supply control signals to the fluidic system 48 via electrically conductive line 56; however, the remote power source 54 can be without a signal generator, if desired, or can supply control signals to the fluidic system 48 in any suitable manner. Similar remote power sources are described in more detail in U.S. Pat. No. 6,947,782 to Schulman et al. which is herein incorporated by reference in its entirety.

Preferably, the remote power source 54 is coupled to a sensor 58 by electrically conductive line 60; however, the remote power source 54 can be coupled to sensor 58 in any suitable manner. The sensor 58 is preferably a tension sensor positioned on the zonules 20 so that the sensor 58 detects the amount of tension present in the zonules 20; however, the sensor 58 can be a wireless signal sensor, a neurotransmitter sensor, a chemical sensor, a pressure sensor or any other suitable sensor type and/or can be positioned in or near the ciliary muscle 22, at or near the nerve controlling the ciliary muscle 22, in the capsular bag 18 or in any other suitable location. Preferably, the sensor 58 detects the eye's attempt to cause its lens to accommodate; however, the sensor 58 can detect a manual attempt to accommodate the lens 38 (e.g., input through a wireless controller) or any other suitable input. The information detected at the sensor 58 is relayed to the remote power source 54 via line 60, and the signal generator of the remote power source 54 generates a signal in accordance with the information. The signal is sent to the fluidic system 48, which adjusts the fluidic pressure in one or more of the chambers 40 accordingly. Thus, the eye's natural attempts to focus will result in accommodation of lens 38. Response of lens 38 may vary from that of the natural lens; however, the neural systems which control the ciliary muscle 22 (and therefore the tension on the zonules 20), are provided with feedback from the optic nerve and visual neural pathways. As a result, the neural system can learn and adjust to the characteristics of the lens 38.

Figure 6:
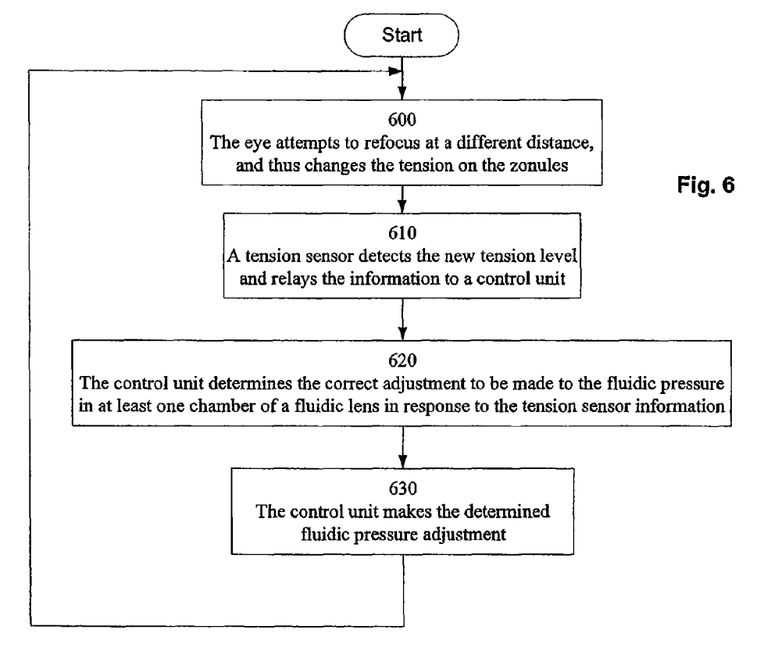
FIG. 6 is a flow chart of the process of accommodation in accordance with one embodiment of the present invention.

The process of accommodation in accordance with one embodiment is shown in FIG. 6. At step 600, the eye attempts to refocus at a different distance, and thus changes the tension on the zonules. At step 610, a tension sensor detects the new tension level and relays the information to a control unit. The control unit preferably includes a remote power source and a fluidic system; however, the control unit can include any suitable devices. At step 620, the control unit determines the correct adjustment to be made to the fluidic pressure in at least one chamber of a fluidic lens in response to the tension sensor information. At step 630, the control unit makes the determined fluidic pressure adjustment and the process repeats at step 600.

Figure 7:
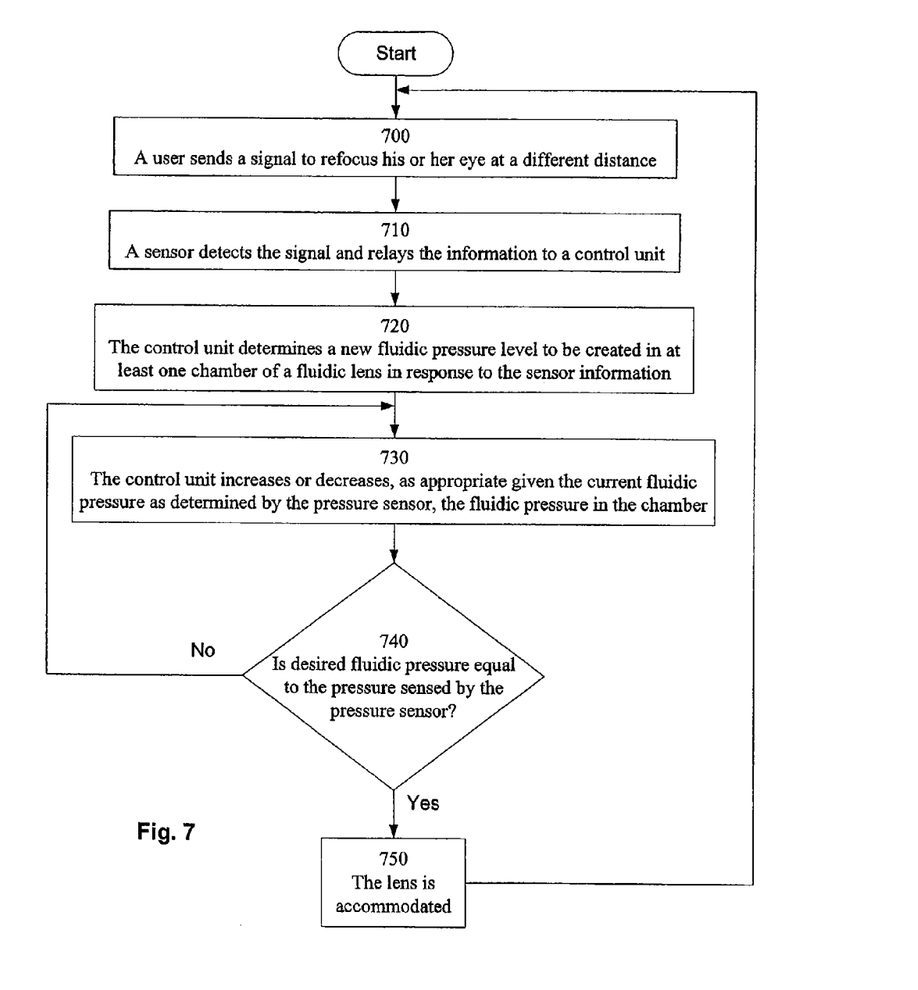
FIG. 7 is a flow chart of the process of accommodation in which the fluidic system includes a pressure sensor for sensing the pressure in at least one of the chambers in accordance with one embodiment of the present invention.

Another process of accommodation in accordance with another embodiment in which the fluidic system includes a pressure sensor for sensing the pressure in at least one of the chambers is shown in FIG. 7. At step 700, a user sends a signal to refocus his or her eye at a different distance. Preferably, the signal is sent wirelessly; however, the signal can be sent in any suitable manner. Further, the signal preferably includes information corresponding to the desired different distance; however, the signal can include information indicating only that the desired distance is closer or farther or any other suitable information. At step 710, a sensor detects the signal and relays the information to a control unit. The control unit preferably includes a remote power source and a fluidic system; however, the control unit can include any suitable devices. At step 720, the control unit determines a new fluidic pressure level to be created in at least one chamber of a fluidic lens in response to the sensor information. At step 730, the control unit increases or decreases, as appropriate given the current fluidic pressure as determined by the pressure sensor, the fluidic pressure in the chamber. At step 740 it is determined whether the desired fluidic pressure is equal to the pressure sensed by the pressure sensor. If the desired fluidic pressure is equal to the pressure sensed by the pressure sensor, at step 750, the lens is accommodated and the process repeats at step 700. If the desired fluidic pressure is not equal to the pressure sensed by the pressure sensor, the process repeats at step 730.

Figure 8:
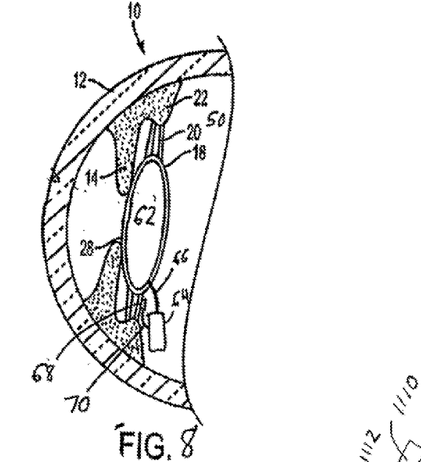
FIG. 8 is a side elevational view in section of the eye shown in FIG. 3 in which a replacement lens is positioned in the capsular bag and a power unit is positioned in the posterior chamber.

FIG. 8 illustrates an alternative accommodating lens 62. Lens 62 responds to electrical stimulation by changing its focal length. Similar to lens 38, lens 62 is preferably placed within the capsular bag 18; however, the lens 62 can be placed in the posterior chamber 50, in place of the capsular bag 18, within the cornea 12, on the surface of the eye or in any other suitable location. Further, it should be noted that any suitable section of the capsular bag can be removed, including but not limited to an anterior portion or a posterior portion around the main optical axis of the eye. If the lens 62 is placed within the capsular bag 18, the capsular bag can assist with accommodation; however, it is not necessary for the capsular bag 18 to assist with accommodation. Lens 62 may have one or more chambers that are at least partly filled with a fluid or other substance; however, lens 62 is not required to have a chamber.

Preferably, lens 62 is a fluid lens that alters its focal length by changing its shape; however lens 62 can be any suitable type of lens and can change its focal length in any suitable manner. The lens 62 preferably includes two immiscible (i.e., non-mixing) fluids of different refractive index (or other suitable optical property); however, the lens 62 is not required to include two immiscible fluids of different refractive index. Preferably, one of the immiscible fluids is an electrically conducting aqueous solution and the other an electrically non-conducting oil, contained in a short tube with transparent end caps; however, the immiscible fluids can be any suitable fluids and can be contained in any suitable container. The internal surfaces of the tube wall and one of its end caps are preferably coated with a hydrophobic coating that causes the aqueous solution to form itself into a hemispherical mass at the opposite end of the tube, where it acts as a spherically curved lens; however, the hydrophobic coating is not required and, if present, can be arranged in any suitable manner. Further, the coating can include any suitable material, including hydrophilic substances.

Preferably, the shape of the lens 62 can be adjusted by applying an electric field across the hydrophobic coating such that it becomes less hydrophobic (a process called "electrowetting" that results from an electrically induced change in surface-tension); however, the shape of the lens 62 can be adjusted by applying an electric field across any suitable portion of the lens 62. Preferably, as a result of this change in surface-tension, the aqueous solution begins to wet the sidewalls of the tube, altering the radius of curvature of the meniscus between the two fluids and hence the focal length of the lens. Increasing the applied electric field can preferably cause the surface of the initially convex lens to become less convex, substantially flat or concave; however increasing the applied electric field can cause the surface of the lens to change in any suitable manner. Preferably, decreasing the applied electric field has the opposite effect, enabling the lens 62 to transition smoothly from being convergent to divergent, or vice versa, and back again repeatably.

The lens 62 can measure 3 mm in diameter by 2.2 mm in length; however the lens 62 can have any suitable dimensions. The focal range of the lens 62 can be any suitable range and can extend to infinity. Further, switching over the full focal range can occur in less than 10 ms or any other suitable amount of time. Preferably, lens 62 is controlled by a DC voltage and presents a capacitive load; however, the lens 62 can be controlled by any suitable voltage and operate with any suitable electrical properties.

Lens 62 is electrically coupled to a power source 64 by electrically conductive line 66; however, lens 62 can be coupled to power source 64 in any suitable manner. Preferably, power source 64 is rechargeable through induction or other suitable means such as generating and storing electrical energy using eye and/or head movement to provide the energy to drive the generator; however, the power source 64 can be non-rechargeable, if desired. Similar to remote power source 54, the power source 64 is preferably located in the posterior chamber 50; however, the power source 64 can be positioned outside the eye (e.g., under the scalp, within a sinus cavity, under the cheek, in the torso or in any other suitable location), within the sclera, between the sclera and the choroids or any other suitable location. Further, the power source 64 is preferably positioned such that it is not in the visual pathway. The power source 64 preferably includes a signal generator which can supply current to the lens 62 via electrically conductive line 66; however, the power source 64 can be without a signal generator, if desired, or can supply control signals to the lens 62 in any suitable manner.

Preferably, the power source 64 is coupled to a sensor 68 by electrically conductive line 70; however, the power source 64 can be coupled to sensor 68 in any suitable manner. The sensor 68 is preferably a tension sensor positioned on the zonules 20 so that the sensor 68 detects the amount of tension present in the zonules 20; however, the sensor 68 can be a wireless signal sensor, a neurotransmitter sensor, a chemical sensor, a pressure sensor or any other suitable sensor type and/or can be positioned in or near the ciliary muscle 22, at or near the nerve controlling the ciliary muscle 22, in the capsular bag 18 or in any other suitable location. Preferably, the sensor 68 detects the eye's attempt to cause its lens to accommodate; however, the sensor 68 can detect a manual attempt to accommodate the lens 62 (e.g., input through a wireless controller) or any other suitable input. The information detected at the sensor 68 is relayed to the power source 64 via line 70, and the signal generator of the power source 64 generates a signal in accordance with the information. The signal is sent and passed through the lens 62, which preferably changes shape as a result of the electrical current flowing through it; however, the lens 62 could change its index of refraction in response to the electrical current flowing through it or change its focal length in any other suitable manner. Preferably, line 70 includes two separate electrical pathways that electrically couple to lens 62 at different, preferably substantially opposite, locations so that one of the pathways can serve as a ground wire; however, the lens 62 can be grounded in any other suitable manner to enable current supplied via line 70 to flow through the lens 62. As a result, similar to lens 38, the eye's natural attempts to focus will result in accommodation of lens 62. Response of lens 62 may vary from that of the natural lens; however, as with lens 38, the neural systems which control the ciliary muscle 22 (and therefore the tension on the zonules 20), are provided with feedback from the optic nerve and visual neural pathways. As a result, the neural system can learn and adjust to the characteristics of the lens 62.

Figure 9:
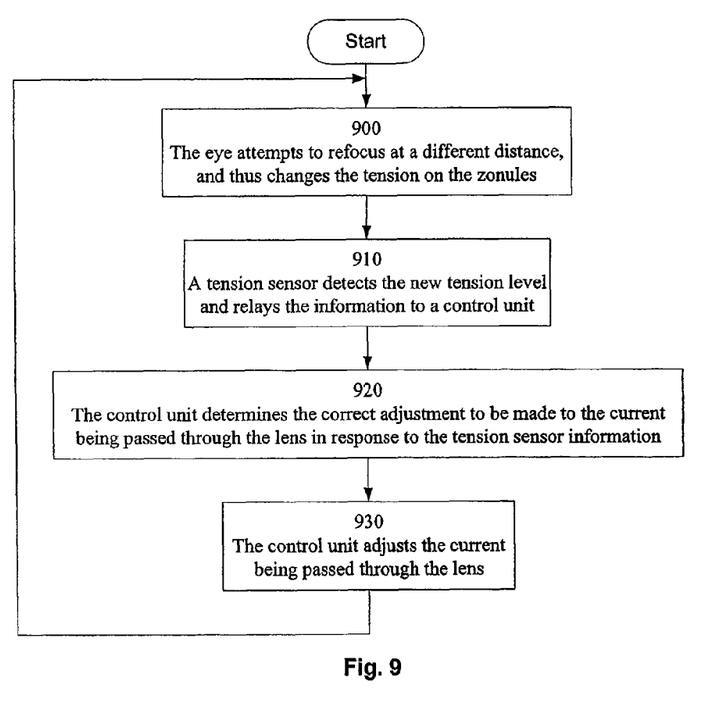
FIG. 9 is a flow chart of the process of accommodation in response to electrical signals in accordance with one embodiment of the present invention.

The process of accommodation in response to electrical signals in accordance with one embodiment is shown in FIG. 9. At step 900, the eye attempts to refocus at a different distance, and thus changes the tension on the zonules. At step 910, a tension sensor detects the new tension level and relays the information to a control unit. The control unit preferably includes a power source; however, the control unit can include any suitable devices. At step 920, the control unit determines the correct adjustment to be made to the current being passed through the lens in response to the tension sensor information. At step 930, the control unit adjusts the current being passed through the lens and the process repeats at step 900.

Figure 10:
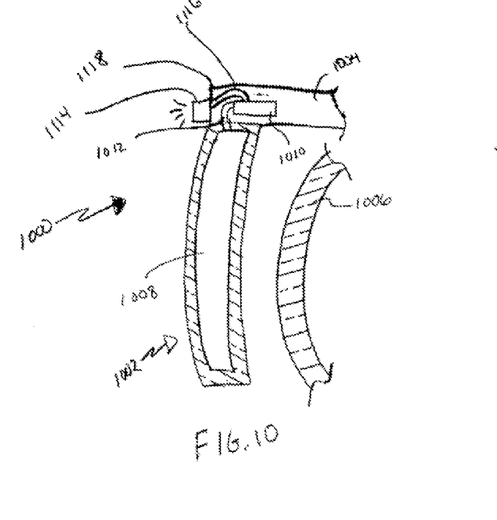
FIG. 10 is a side view in section of another embodiment of the present invention, showing the adjustable lens positioned relative to the eye.
Figure 11:
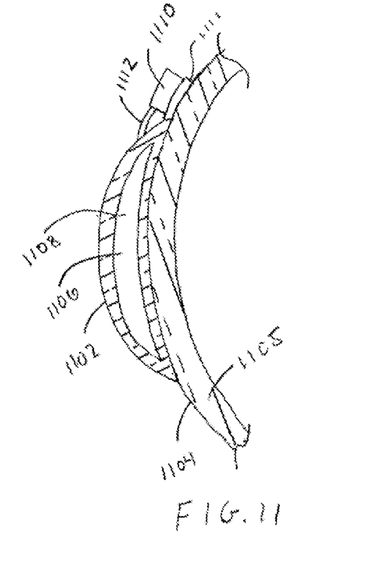
FIG. 11 is a side view in section of another embodiment of the present invention, showing the adjustable lens as a contact lens.

In another embodiment, as illustrated in FIGS. 10-11, the present invention can be used in an external lens. For example, the lens can be configured to be used with spectacles (FIG. 10) or as a contact lens FIG. 11). The embodiments of FIG. 10-11 are configured to correct refractive errors in the eye. For example, the present embodiments can correct at least myopia, hyperopia and astigmatism. Furthermore, since these embodiments (as discussed in more detail below) can have their refractive properties altered, they are multi-focal lenses. Thus, these lenses can correct, among other disorders, presbyopia, or any combination of disorders.

When configured to be used in conjunction with spectacles 1000, lens 1002 is preferably coupled to a frame 1004 that positions the lens 1002 relative to the cornea 1006 of the eye in any suitable manner. As with previous embodiments, the lens 1002 has a chamber or area 1008 (or multiple chambers or areas, if desired) that is configured to hold a fluid or a mixture of fluids or any other suitable substance. Chamber 1008 preferably includes two immiscible (i.e., non-mixing) fluids of different refractive index (or other suitable optical property); however, the chamber 1008 is not required to include two immiscible fluids of different refractive index. Preferably, one of the immiscible fluids is an electrically conducting aqueous solution and the other an electrically non-conducting oil, contained in a short tube with transparent end caps, as described above; however, the immiscible fluids can be any suitable fluids and can be contained in any suitable container. The above description of the fluids is applicable to the present invention.

Preferably, as with the embodiments above, the shape of the lens 1002 can be adjusted by applying an electric field across the hydrophobic coating such that it becomes less hydrophobic (a process called "electrowetting" that results from an electrically induced change in surface-tension); however, the shape of the lens 1002 can be adjusted by applying an electric field across any suitable portion of the lens 1002. Preferably, as a result of this change in surface-tension, the aqueous solution begins to wet the sidewalls of the tube, altering the radius of curvature of the meniscus between the two fluids and hence the focal length of the lens. Increasing the applied electric field can preferably cause the surface of the initially convex lens to become less convex, substantially flat or concave; however increasing the applied electric field can cause the surface of the lens to change in any suitable manner. Preferably, decreasing the applied electric field has the opposite effect, enabling the lens 1002 to transition smoothly from being convergent to divergent, or vice versa, and back again repeatably. Thus, allowing the lens 1002 to repeatably focus on near and/or far objects.

The focal range of the lens 1002 can be any suitable range and can extend to infinity. Further, switching over the full focal range can occur in less than 10 ms or any other suitable amount of time. Preferably, lens 1002 is controlled by a DC voltage and presents a capacitive load; however, the lens 1002 can be controlled by any suitable voltage and operate with any suitable electrical properties.

Lens 1002 is electrically coupled to a power source 1010 by electrically conductive line 1012; however, lens 1002 can be coupled to power source 1010 in any suitable manner. Preferably, power source 1010 is rechargeable through direct electrical current, induction or other suitable means such as generating and storing electrical energy using eye and/or head movement to provide the energy to drive the generator; however, the power source 1010 can be non-rechargeable, if desired. Power source 1010 is preferably located on the frame 1004 of spectacles 1000; however, the power source 1010 can be positioned in any suitable location. The power source 1010 preferably includes a signal generator which can supply current to the lens 1002 via electrically conductive line 1112; however, the power source 1010 can be without a signal generator, if desired, or can supply control signals to the lens 1002 in any suitable manner.

Preferably, the power source 1010 is coupled to a sensor 1114 by electrically conductive line 1116; however, the power source 1010 can be coupled to sensor 1116 in any suitable manner (e.g. wirelessly). The sensor 1114 is preferably a distance sensor positioned on the front 1118 of frame 1004 so that the sensor 1114 detects the distance of an object away from the eye (such as a laser range finder); however, the sensor 1114 can be any suitable sensor type. Preferably, the sensor 1114 is positioned relative to the eye such that it detects the distance a specific object is from the eye and adjusts the lens 1002 accordingly; however, the sensor 1114 can detect a manual attempt to adjust the lens 1002 (e.g., input through a wireless controller or direct push buttons) or any other suitable input. The information detected at the sensor 1114 is relayed to the power source 1010 via line 1116, and the signal generator of the power source 1010 generates a signal in accordance with the information. The signal is sent and passed through the lens 1002, which preferably changes shape as a result of the electrical current flowing through it; however, the lens 1002 could change its index of refraction in response to the electrical current flowing through it or change its focal length in any other suitable manner. Preferably, line 1116 includes two separate electrical pathways that electrically couple to lens 1102 at different, preferably substantially opposite, locations so that one of the pathways can serve as a ground wire; however, the lens 1002 can be grounded in any other suitable manner to enable current supplied via line 1116 to flow through the lens 1002.

Additionally, the lens 1002 can be wirelessly coupled to a sensor, such as sensor 64, described above and adjust based on signals from the cilliary muscles and/or the zonules. Response of lens 1002 may vary from that of the natural lens; however, as with lenses described above, the neural systems which control the ciliary muscle 22 (and therefore the tension on the zonules 20), are provided with feedback from the optic nerve and visual neural pathways. As a result, the neural system can learn and adjust to the characteristics of the lens 1002.

FIG. 11 illustrates another embodiment of the present invention, where the lens 1102 is a contact lens that is positioned on the external surface 1104 of the cornea 1105.

As with lens 1002, lens 1102 includes a chamber or area 1106 (or multiple chambers or areas, if desired) having a fluid 1108 therein. Preferably, fluid 1108 is the same as the fluid described above for lens 1002 and operates in the substantially the same manner; however, any suitable fluid and/or substance or combination thereof can be used.

As described above, lens 1102 is coupled to a power source 1110 via an electrical wire 1112, or by any other suitable means. The power source 1110 is coupled to lens 1102 in any suitable manner (e.g., attached to a protrusion 1111). Power source 1110 and electrical wire 1112 are configured and operate in substantially the same manner as described above for lens 1002. Any description of lens 1002 and power source 1010 is applicable to lens 1102 and power source 1110.

Furthermore, lens 1102 can have a distance sensor (or any other sensor) that is located outside the eye and wirelessly coupled or directly wired to power source 1110, as described above. The sensor can be a sensor coupled to the lens 1102 (or any other suitable place on or adjacent the eye) or it can be located in the eye, and operate in substantially the same manner as sensors described above.

Additionally, both lens 1002 and 1102 can have their respective refractive properties altered in any manner described herein and are not limited the specific descriptions above. For example, lens 1102 and lens 1002 can have their respective refractive properties altered by changing the fluidic pressure as described above.

Figure 12A:
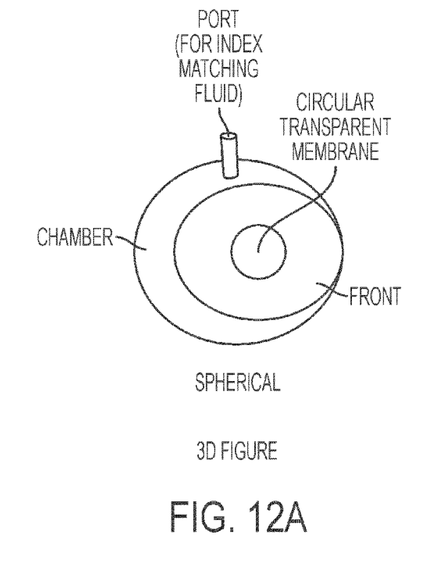
FIGS. 12 and 13 illustrate another embodiment of the present invention in which a device is shown that is capable of correcting all low order aberration of the refractive errors.
Figure 12B:
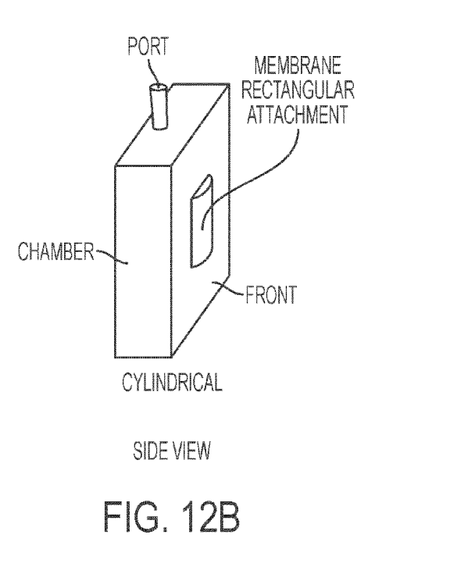
Figure 13:
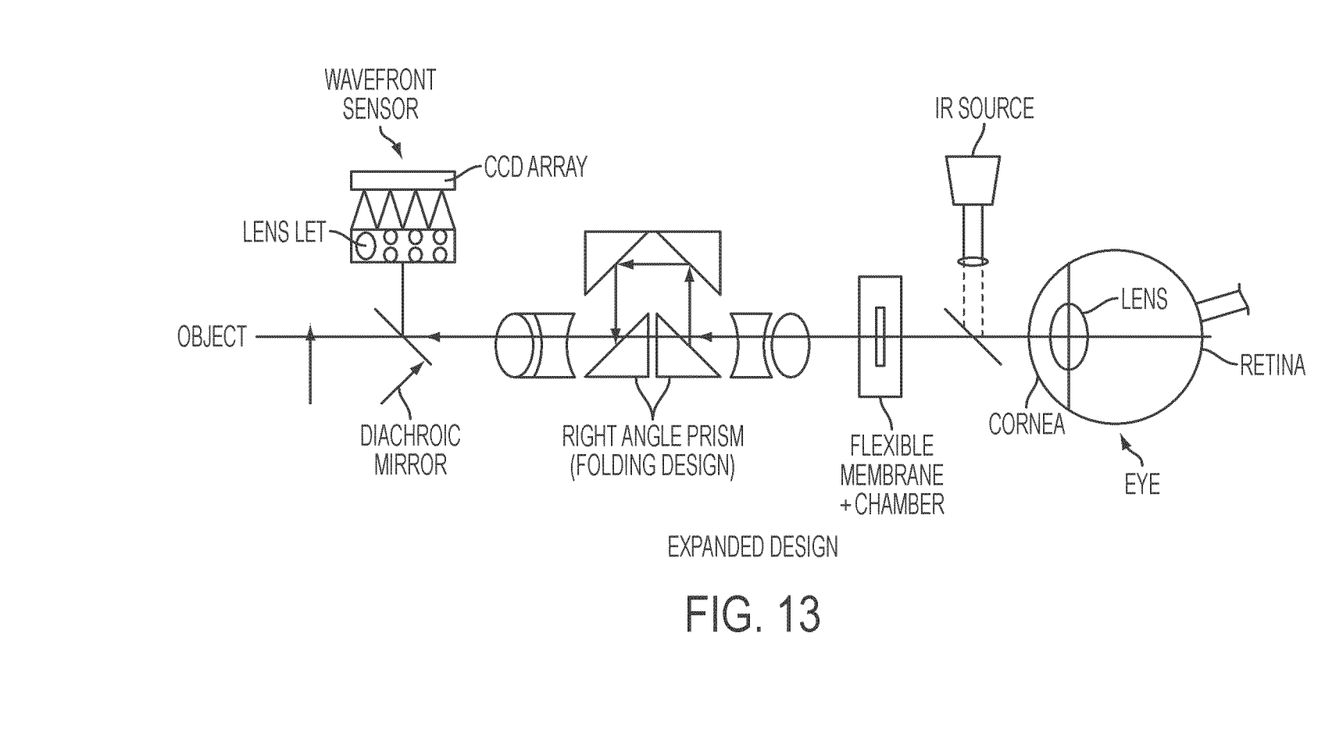

As shown in FIGS. 12 and 13, one embodiment of the automated system of the present invention comprises flexible membrane, similar to the embodiments, described above, attached to a solid chamber where the membrane's surface can be made to act as a positive or negative surface by altering the fluid pressure inside the chamber.

The membrane can be constructed from any transparent elastomeric material. Depending on the membrane's peripheral attachment (e.g. circular) the membrane acts as a spherical (plus or minus 35.00 D) lens or (plus or minus 8.00 D) cylindrical lens when its attachment is rectangular (FIG. 1A-B).

By combining one spherical and two cylindrical lens-membranes, positioned 45 degrees to one another, one can correct all low order aberration of the refractive errors.

Using a non-uniform thickness membrane or an additional lens module one can also correct the higher order aberrations of refractive errors and creation of an achromatic lens. The flexible membrane lens is adjusted to null the wavefront error of the eye.

When this system is combined with a relay telescope, the image of the eye pupil can be projected onto a wavefront sensor via a diachronic mirror to analyze the shape of the wavefront (FIG. 13) while the person sees a near or distant object. The present system eliminates deformable mirrors and scanning parts; therefore it is a compact and stable unit.

The sensor in return corrects automatically all refractive errors of an eye by adding or subtracting fluid from the chamber holding the flexible membrane, thereby adjusting the curvature of the flexible membranes.

The final information is equal to the eye's refractive power of an eye for any given distance. Because of its simple design and light weight of the system both eyes of a person can be corrected simultaneously.

Additional application of this concept besides vision correction and photography includes microscope lenses, operating microscope, a lensometer capable of measuring accurately various focal points (power) of a multifocal lens or a multifocal diffractive lens, liquid crystal lenses etc. known in the art. A combination of the plus and minus flexible membrane lenses can also provide a lightweight telescope. Others include hybrid combination of this technology with diffractive, refractive and liquid crystal lenses.

Figure 14:
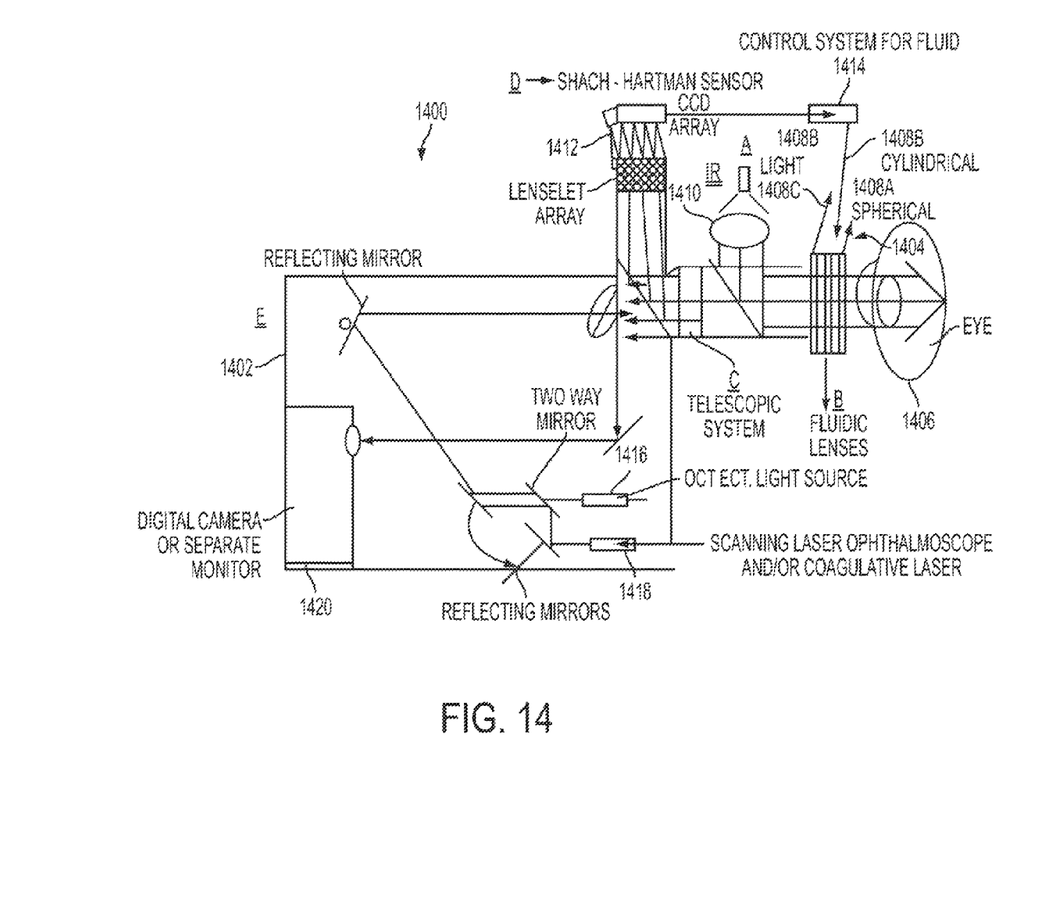
FIG. 14 illustrates another embodiment of the present invention in which a fluidic adaptive optic fundus camera is shown.

FIG. 14 illustrates another embodiment of the present invention. In particular, FIG. 14 illustrates a system 1400 in which a fundus camera 1402 uses a fluidic adaptive optic lens 1404. Adjacent the patient's eye 1406, are the three fluidic lenses 1408A-C. Preferably, one of the fluidic lenses is a spherical lens 1408A, and two of the lenses are cylindrical lenses 1408B and 1408C. However, the system can include any number of suitable lenses. Preferably the cylindrical lenses are positioned at 45 degrees or about 45 degrees to each other, and are disposed behind the spherical lens (i.e., farther from the eye).

The three lens system forms a telescopic system that transmits the light from IR light 1410 reflected from the eye and through the three lenses to a Shack-Hartmann sensor 1412. The Shack-Hartman sensor is connected to control system 1414 through a CCD array. The Shack-Hartman sensor and the control system controls the amount of fluid injected and/or removed in the three fluidic lenses. Preferably, the control system includes (or is in communication with) a pump (not shown) which injected and withdraws fluid from a container (not shown). By injecting and withdrawing fluid from the lenses, high and low order aberrations are eliminated prior to the photography, since the fluidic lenses are capable of adjusting the specific needs of the eye, in the same manner as described above.

Fundus camera 1402 is preferably equipped with white flush or a scanning laser ophthalmoscope or various lasers with different wavelengths from ultraviolet to infra red wave length to obtain various visual information from the retina, choroid and optic nerve head. An Optical coherence tomography (OCT) 1416 or a laser can replace the scanning laser 1418 (or coagulative laser) to obtain two or three dimensional histological images from the eye structures or the laser can perform a precise coagulation of the retina along with the OCT images.

The fundus camera 1402 is also connected a digital camera 1420 and/or a visualization monitor. Therefore, the images captured by the fundus camera can be viewed in real time or captured for viewing at a later time.

Additionally, the camera position cam be moved into any desired position by a two way mirror that is positioned behind the fluidic lens.

The present system results in a compact, light weight, precise and inexpensive advanced camera system eliminating the need for the complex prior technology which uses deformable mirrors.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A fundus camera, comprising:
   three fluidic lenses, each of the three fluidic lenses having a chamber that receives a fluid therein, an amount of the fluid being inserted into the chamber or removed from the chamber by a fluid control system, such that the shape of each of the three fluidic lenses is changed based on the amount of fluid therein, one of the three fluidic lenses comprising a spherical lens with a circular transparent membrane and at least another of the plurality of fluidic lenses comprising a cylindrical lens with a rectangular transparent membrane, the spherical lens being disposed in front of the cylindrical lens relative to a path of light being reflected back from the eye such that the reflected light enters the spherical lens prior to entering the cylindrical lens;
   a light source configured to direct light into an eye;
   a refractive or diffractic telescopic system configured to transmit the light, which is reflected back from the eye and through the three fluidic lenses, to a Shack-Hartmann sensor;
   the Shack-Hartmann sensor by means of the fluid control system automatically controlling the amount of the fluid in the chamber of each of the three fluidic lenses, so as to be capable of correcting refractive errors in the eye; and
   a multifunction camera configured to acquire precise fundus images of the eye.

2. The fundus camera of claim 1, further comprising at least one of an optical coherence tomography, a scanning laser, and a coagulative or ablative laser.

3. The fundus camera of claim 1, wherein the three fluidic lenses further include another cylindrical lens.

4. The fundus camera of claim 3, wherein the cylindrical lenses are positioned at about 45 degrees relative to each other, and are disposed so as to be farther from the eye than the spherical lens.

5. The fundus camera of claim 1, wherein the multifunction camera is a digital camera.

6. The fundus camera of claim 5, wherein the chambers of each of the three fluidic lenses are configured to have the fluid injected thereinto and withdrawn therefrom so as to be capable of eliminating high and low order aberrations prior to the digital camera acquiring the fundus images of the eye.

7. The fundus camera of claim 1, wherein the Shack-Hartmann sensor is operatively coupled to the fluid control system by means of a charge-coupled device (CCD) array.

8. The fundus camera of claim 1, wherein a lenslet array is disposed in a path of the reflected light entering the Shack-Hartmann sensor.

9. The fundus camera of claim 1, further comprising a coagulative laser configured to generate a coagulative laser beam; and
   a plurality of reflective mirrors and a two-way mirror disposed in a path of the coagulative laser beam, the plurality of reflective mirrors and the two-way mirror configured to direct the coagulative laser beam to the eye, the two-way mirror being disposed between a first of the plurality of reflective mirrors and a second of the plurality of reflective mirrors.

10. A fundus camera, comprising:
    a light source configured to direct light into an eye;
    a plurality of fluidic lenses disposed in a path of the light emanating from the light source, each of the plurality of fluidic lenses having a respective chamber that receives a fluid therein;
    a fluid control system operatively coupled to each of the plurality of fluidic lenses, the fluid control system configured to insert an amount of the fluid into the respective chamber of each of the plurality of fluidic lenses, or remove an amount of the fluid from the respective chamber of each of the plurality of fluidic lenses, in order to change the shape of each of the plurality of fluidic lenses in accordance with the amount of fluid therein;
    a Shack-Hartmann sensor operatively coupled to the fluid control system, the Shack-Hartmann sensor by means of the fluid control system configured to automatically control the amount of the fluid in the respective chamber of each of the plurality of fluidic lenses, so as to be capable of correcting refractive errors in the eye;
    a refractive or diffractic telescopic system disposed in a path of the light between the plurality of fluidic lenses and the Shack-Hartmann sensor, the refractive or diffractic telescopic system configured to transmit the light that is reflected back from the eye to the Shack-Hartmann sensor;
    a multifunction camera configured to acquire precise fundus images of the eye;
    a coagulative laser configured to generate a coagulative laser beam; and a plurality of reflective mirrors and a two-way mirror disposed in a path of the coagulative laser beam, the plurality of reflective mirrors and the two-way mirror configured to direct the wherein the plurality of fluidic lenses include a spherical lens and first and second cylindrical lenses.

11. The fundus camera of claim 10, further comprising an optical coherence tomography device configured to acquire two or three dimensional histological images of the eye.

12. The fundus camera of claim 10, wherein the first and second cylindrical lenses are positioned at about 45 degrees relative to each other, and are disposed so as to be farther from the eye than the spherical lens.

13. The fundus camera of claim 10, wherein the Shack-Hartmann sensor is operatively coupled to the fluid control system by means of a charge-coupled device (CCD) array.

14. The fundus camera of claim 10, wherein a lenslet array is disposed in a path of the reflected light entering the Shack-Hartmann sensor.

15. The fundus camera of claim 10, wherein the spherical lens comprises a circular transparent membrane and each of the first and second cylindrical lenses comprises a rectangular transparent membrane.

16. A fundus camera, comprising:
a light source configured to direct light into an eye;
a plurality of fluidic lenses disposed in a path of the light emanating from the light source, each of the plurality of fluidic lenses having a respective chamber that receives a fluid therein, one of the plurality of fluidic lenses comprising a spherical lens and at least another of the plurality of fluidic lenses comprising a cylindrical lens, the spherical lens being disposed in front of the cylindrical lens relative to a path of light being reflected back from the eye such that the reflected light enters the spherical lens prior to entering the cylindrical lens;
a fluid control system operatively coupled to each of the plurality of fluidic lenses, the fluid control system configured to insert an amount of the fluid into the respective chamber of each of the plurality of fluidic lenses, or remove an amount of the fluid from the respective chamber of each of the plurality of fluidic lenses, in order to change the shape of each of the plurality of fluidic lenses in accordance with the amount of fluid therein;
a Shack-Hartmann sensor operatively coupled to the fluid control system, the Shack-Hartmann sensor by means of the fluid control system configured to automatically control the amount of the fluid in the respective chamber of each of the plurality of fluidic lenses, so as to be capable of correcting refractive errors in the eye;
a refractive or diffractic telescopic system disposed in a path of the light between the plurality of fluidic lenses and the Shack-Hartmann sensor, the refractive or diffractic telescopic system configured to transmit the light that is reflected back from the eye to the Shack-Hartmann sensor;
a multifunction camera configured to acquire precise fundus images of the eye;
a coagulative laser configured to generate a coagulative laser beam; and
a plurality of reflective mirrors and a two-way mirror disposed in a path of the coagulative laser beam, the plurality of reflective mirrors and the two-way mirror configured to direct the coagulative laser beam to the eye.

17. The fundus camera of claim 16, wherein the plurality of fluidic lenses comprises another cylindrical lens, the cylindrical lenses being positioned at about 45 degrees relative to each other, and each of the cylindrical lenses being disposed behind the spherical lens relative to a path of light being reflected back from the eye such that the reflected light enters the spherical lens prior to entering either of the cylindrical lens.

18. The fundus camera of claim 16, wherein the Shack-Hartmann sensor is operatively coupled to the fluid control system by means of a charge-coupled device (CCD) array.

19. The fundus camera of claim 16, wherein a lenslet array is disposed in a path of the reflected light entering the Shack-Hartmann sensor.

* * * * *